United States Patent [19]

Cresswall

[11] 4,035,850
[45] July 19, 1977

[54] METHOD AND APPARATUS FOR INSERTING SOFT PROSTHESIS

[75] Inventor: Thomas A. Cresswall, Saginaw, Mich.

[73] Assignee: Thomas A. Cresswall, Saginaw, Mich.

[21] Appl. No.: 730,661

[22] Filed: Oct. 7, 1976

[51] Int. Cl.$^2$ .......................... A61F 1/24; A61F 1/00; A61B 17/00
[52] U.S. Cl. ................................................. 3/36; 3/1; 128/303 R; 128/262
[58] Field of Search ...................... 3/36, 1; 128/303 R, 128/262

[56] References Cited

U.S. PATENT DOCUMENTS

| 3,416,160 | 12/1968 | Arion | 3/36 |
| 3,516,406 | 6/1970 | Jensen | 128/262 X |
| 3,860,969 | 1/1975 | Arion | 3/36 |
| 3,883,902 | 5/1975 | Lynch | 3/36 |
| 3,919,724 | 11/1975 | Sanders et al. | 3/36 |

FOREIGN PATENT DOCUMENTS

| 106,568 | 11/1899 | Germany | 128/262 |

*Primary Examiner*—Ronald L. Frinks
*Attorney, Agent, or Firm*—Learman & McCulloch

[57] ABSTRACT

A method and apparatus for inserting a soft pliable prosthesis, such as a mammary prosthesis, into a human body through an incision. A prosthesis to be inserted is contained in an open mouthed inner bag of flexible fluid impervious sheet material and in a preferred form of the invention, a second outer open mouthed bag of similar material is sealingly joined to the inner bag at the mouths of the bags by means of a ring member seal. The outer bag carries a charge of fluid. The ring member is provided with a flange which may be seated in an open incision, and upon squeezing of the outer bag, the pressure applied to the fluid in the space between the two bags everts the inner bag through the ring member to carry the prosthesis contained therein to the desired position within the body.

8 Claims, 4 Drawing Figures

METHOD AND APPARATUS FOR INSERTING SOFT PROSTHESIS

BACKGROUND OF THE INVENTION

The present invention is especially concerned with an apparatus for inserting or implanting a prefilled mammary prosthesis of a well-known type in which a shaped flexible container is filled with a silicone gel prior to implanting. Implanting of this type of prosthesis not only requires manual handling with the attendent possibility of contamination, but also presents the possibility of rupturing the gel enclosing envelope during the process of placing it in position. The present invention is especially designed to provide a sanitary apparatus in which the prosthesis is packaged in a container in a manner such that the prosthesis can be expelled from the container by an evenly applied fluid pressure and direct handling of the prosthesis itself is not required.

In a pre-examination search made through prior art the following patents were cited: U.S. Pat. Nos. 3,919,724; 3,883,902; 3,860,969; 3,852,833.

SUMMARY OF THE INVENTION

The method and apparatus of the present invention involve the employment of an open mouthed double walled container formed by inner and outer bags or receptacles of a fluid impervious material. In a preferred embodiment the mouths of two flexible bags are commonly sealed to each other by a ring member to define a closed fluid-containing chamber between the body portions of the two bags. A prosthesis to be implanted is contained within the inner bag, whose mouth and the central opening of the sealing ring member are of a size sufficient to easily pass the prosthesis. The ring member is provided with an axially projecting flange.

In use, the unit is placed in registry with a surgical incision by inserting the flange of the ring member into the incision. By manually squeezing the outer bag, the fluid contained in the chamber between the two bags everts the inner bag through its mouth and the central opening of the ring member, the inner bag carrying the prosthesis with it and inserting the prosthesis through the opening of the incision into position within the body. The forces applied to the prosthesis during this insertion take the form of an evenly distributed fluid pressure force.

Other objects and features of the invention will become apparent by reference to the following specification and to the drawings.

IN THE DRAWINGS

Figure 4:
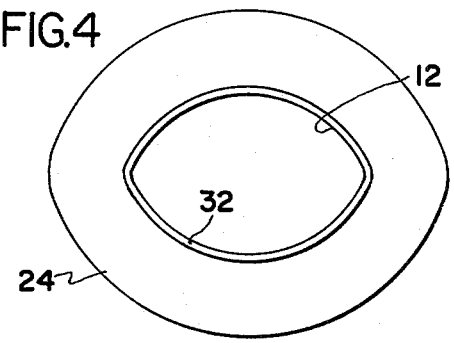
FIG. 4 is a top plan view of the device.
Figure 1:
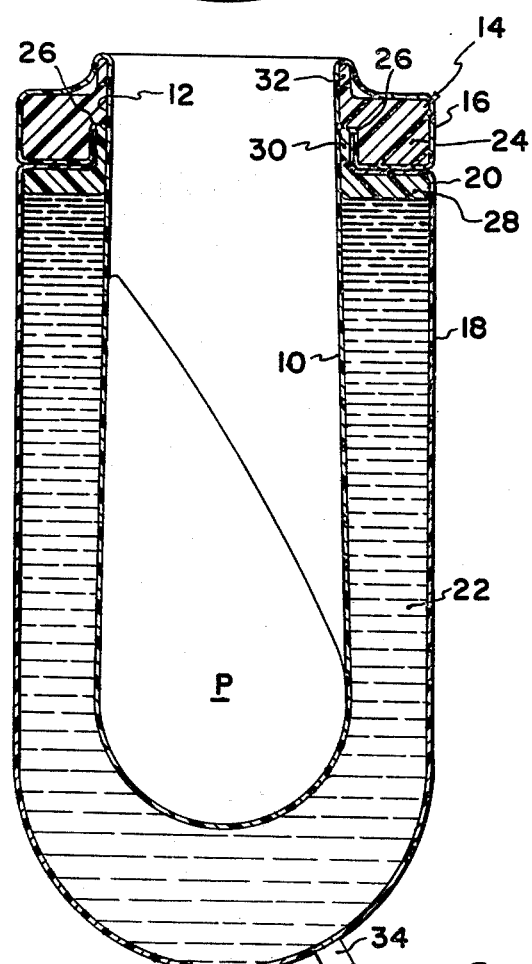
FIG. 1 is a cross sectional view of an apparatus embodying the present invention.

Referring particularly to FIG. 1, apparatus embodying the present invention includes a first open mouthed bag 10 which is formed from a relatively thin and flexible fluid impervious material. The bag is adapted to contain a prefilled mammary prosthesis P of well-known construction such as shown in the patents listed heretofor which are incorporated herein by reference. Such prostheses comprise generally soft, pliable, medical grade, silicone fabric bags of teardrop shape filled with an inert, usually silicone, gel. The bags thus may be described as organosilocane copolymer material filled with a suitable gel such as set forth in U.S. Pat. No. 3,665,520. The upper end of the bag, as viewed in FIG. 1, is passed upwardly through the central opening 12 of a ring member assembly designated generally 14 and then turned back downwardly over the exterior periphery of the ring member assembly as at 16. A second bag 18 of a similar fluid type flexible sheet material receives and encloses the major portion of the inner bag 10 and passes upwardly along and around the outer periphery of the ring assembly 14 as at 20.

Ring assembly 14 functions to peripherally seal the two plastic film bags 10 and 18 to each other around the mouth portions of the respective bags to define an enclosed fluidtype chamber 22 between the two bags. Any of several types of sealing ring assemblies 14 may be employed. In the form shown in the drawings assembly 14 includes an upper member 24 formed with a downwardly opening groove 26 around its inner periphery and a lower member 28 having an upwardly projecting flange 30 around its inner periphery dimensioned to snugly seat with a tight press fit in groove 26 of the upper member. The mouth portions of inner bag 10 and outer bag 18 are sealingly clamped between the upper and lower ring member 24, 28 when the ring member is so assembled. The ring assembly 14 is thus completely enclosed within the bags at all times and is also sealed from contact with the prosthesis P by the inner bag. The upper ring member 24 is formed with an axially projecting flange 32 around its inner periphery for a purpose described hereinafter.

Chamber 22 is filled with a charge of fluid which may take either the form of a liquid, such as a saline solution, or a gas such as air under pressure. For filling purposes outer bag 18 may be provided with a self-sealing gland such as 34 to receive a needle of a syrings S (FIG. 1) through which liquid or gas may be supplied to chamber 22. In the usual case, it is contemplated that chamber 22 will be filled with fluid at the time the device is assembled under sterile conditions and the filled device, containing the prosthesis, will then be packaged in a sealed sterile envelope until the device is ready to be used.

Figure 2:
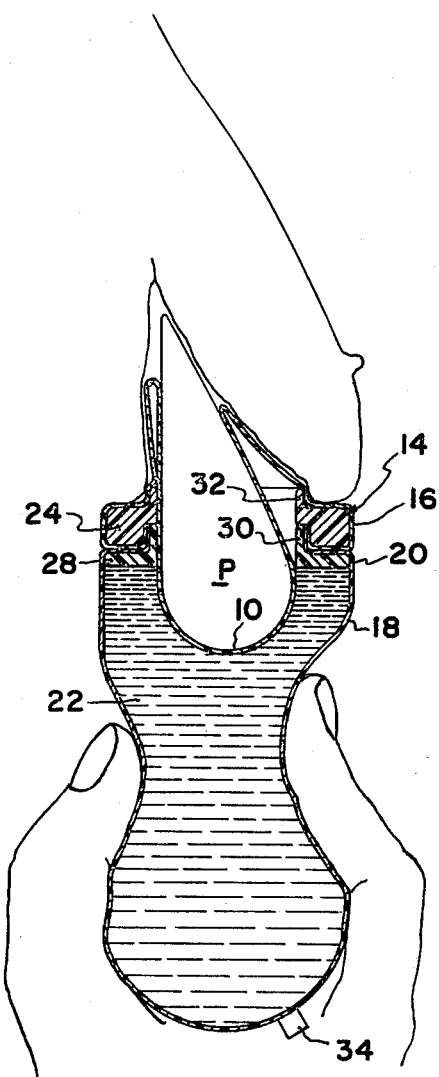
FIG. 2 is a cross sectional view of the apparatus of FIG. 1 during an inserting operation.
Figure 3:
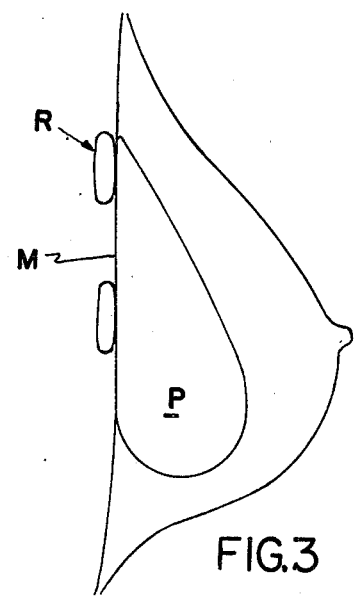
FIG. 3 is a view similar to FIG. 2 showing the prosthesis in position.

In FIG. 2 the device is shown in use with the prosthesis partially inserted in the typical incision which is indicated by the points $a$, $b$. As best seen in FIG. 2, the device is placed in registry with the incision, preferably with the flange 32 of ring assembly 14 inserted slightly into the incision itself. Once the device has been placed in registry with the incision the prosthesis may be inserted through the opened incision simply by manually squeezing outer bag 18 to apply pressure to the fluid within chamber 22. The pressure exerted upon the fluid within chamber 22 is transmitted to the flexible wall of bag 10 and acts to evert bag 10 through the central opening 12 of ring assembly 14, carrying with it prosthesis P in the fashion shown in FIG. 2. The prosthesis is moved, in the eversion process to the position shown in FIG. 3 adjacent the musculature M surrounding rib cage R.

Alternatively, instead of manually squeezing outer bag 18 in the fashion shown in FIG. 2, a syringe needle can be inserted through gland 34 as in the filling step described above and additional fluid can be pumped by the syringe into chamber 22 to accomplish the insertion step described above.

While one exemplary form of the device and two alternative methods of use have been described, it will be apparent to those skilled in the art that modification to the exemplary forms disclosed may be made. Therefore, the foregoing description is to be considered exemplary rather than limiting, and the true scope of the invention is that defined in the following claims.

I claim:

1. The method of inserting a prosthesis, such as a soft, pliable mammary prosthesis or the like, into a human body via an incision comprising the steps of holding the mouth of a flexible walled fluid impervious bag containing the prosthesis in registry with an opened incision, and applying fluid pressure to the exterior of the bag to at least partially evert the bag through its mouth and said incision to carry said prosthesis inwardly through said incision.

2. The method defined in claim 1 wherein said bag is enclosed within a second bag of similar material sealingly enjoined around the periphery of its mouth to the mouth of the prosthesis containing bag and having a charge of fluid, and the step of applying fluid pressure consists of manually squeezing said second bag to apply a uniform pressure.

3. Apparatus for inserting a prosthesis, such as a soft, pliable mammary prosthesis or the like, into a human body via an incision comprising a first open mouthed fluid container, an open mouthed inner bag of flexible fluid impervious material received within said first container, sealing means sealing said bag to said first container around the periphery of the mouth, said bag and said first container defining an enclosed fluid chamber surrounding the exterior of said bag, and a prosthesis located within the interior of said bag and adapted to pass through the mouths of said first container and said bag when a charge of fluid contained in said chamber is compressed to evert said bag through its mouth to carry the prosthesis outwardly through the mouth of said first chamber.

4. The invention defined in claim 3 wherein said first container is a bag of flexible fluid impervious sheet material having an internal volume greater than that of said inner bag.

5. The invention defined in claim 3 wherein said sealing means comprises a ring member having a central opening capable of passing said prosthesis.

6. The invention of claim 5 wherein both of said bags enclose said ring member, said inner bag passing from the outer periphery around one end of said ring member and thence through the opening of said ring member into the interior of said second bag.

7. The invention defined in claim 5 wherein said ring member includes a spout forming flange extending around the periphery of said opening and projecting from said ring member axially outwardly away from said second bag.

8. The invention defined in claim 3 in which a charge of fluid of a volume sufficient to evert said bag is contained in said chamber.

* * * * *